United States Patent [19]

Hentschel et al.

[11] 4,281,123

[45] * Jul. 28, 1981

[54] PROCESS FOR INTRODUCING THREE SUBSTITUENTS IN CYANURIC CHLORIDE

[75] Inventors: Klaus Hentschel, Kalmthout, Belgium; Friedrich Bittner, Bad Soden, Fed. Rep. of Germany

[73] Assignee: Deutsche Gold- und Silber-Scheideanstalt vormals Roessler, Frankfurt, Fed. Rep. of Germany

[ * ] Notice: The portion of the term of this patent subsequent to Jun. 23, 1998, has been disclaimed.

[21] Appl. No.: 94,873

[22] Filed: Nov. 16, 1979

[30] Foreign Application Priority Data

Nov. 20, 1978 [DE] Fed. Rep. of Germany ....... 2850338

[51] Int. Cl.[3] .................. C07D 251/46; C07D 251/52; C07D 251/66; C07D 251/70

[52] U.S. Cl. .................................... 544/194; 544/197; 544/208; 544/210; 544/211; 544/213; 544/219; 544/113; 544/212; 544/209; 544/198

[58] Field of Search ............... 544/194, 211, 212, 219, 544/113, 197, 208, 210, 213, 209, 198

[56] References Cited

U.S. PATENT DOCUMENTS 3,925,377 12/1975 Geiger et al. ........................ 260/248

FOREIGN PATENT DOCUMENTS 1670528 4/1970 Fed. Rep. of Germany .
1670731 12/1970 Fed. Rep. of Germany .
1670585 2/1972 Fed. Rep. of Germany .
2332636 1/1975 Fed. Rep. of Germany .
1239784 7/1960 France .

OTHER PUBLICATIONS

Ullmann, Enzyklopadie der Technischen Chemie, 3rd Edition, 1954, vol. 1, pp. 743-744 and 769-770.

*Primary Examiner*—John M. Ford
*Attorney, Agent, or Firm*—Cushman, Darby & Cushman

[57] ABSTRACT

Three substituents are introduced into cyanuric acid in the presence of an acid binding agent by working in a manner permitting high mixing and therefore high reaction velocities and permitting high throughputs in small tubular containers by introducing liquid cyanuric chloride through a nozzle in the upper portion of the mixing apparatus in countercurrent flow to upwardly flowing reactants (and acid binding agent) introduced from at least one lower nozzle above a breast shaped constriction in the lower, open portion of the apparatus. The process can be carried out at normal, reduced or elevated pressure.

28 Claims, 3 Drawing Figures

PROCESS FOR INTRODUCING THREE SUBSTITUENTS IN CYANURIC CHLORIDE

BACKGROUND OF THE INVENTION

The present invention is directed to a process making it possible to replace the three chlorine atoms of cyanuric chloride by three identical substituents in a very simple and effective manner.

SUMMARY OF THE INVENTION

Figure 1:
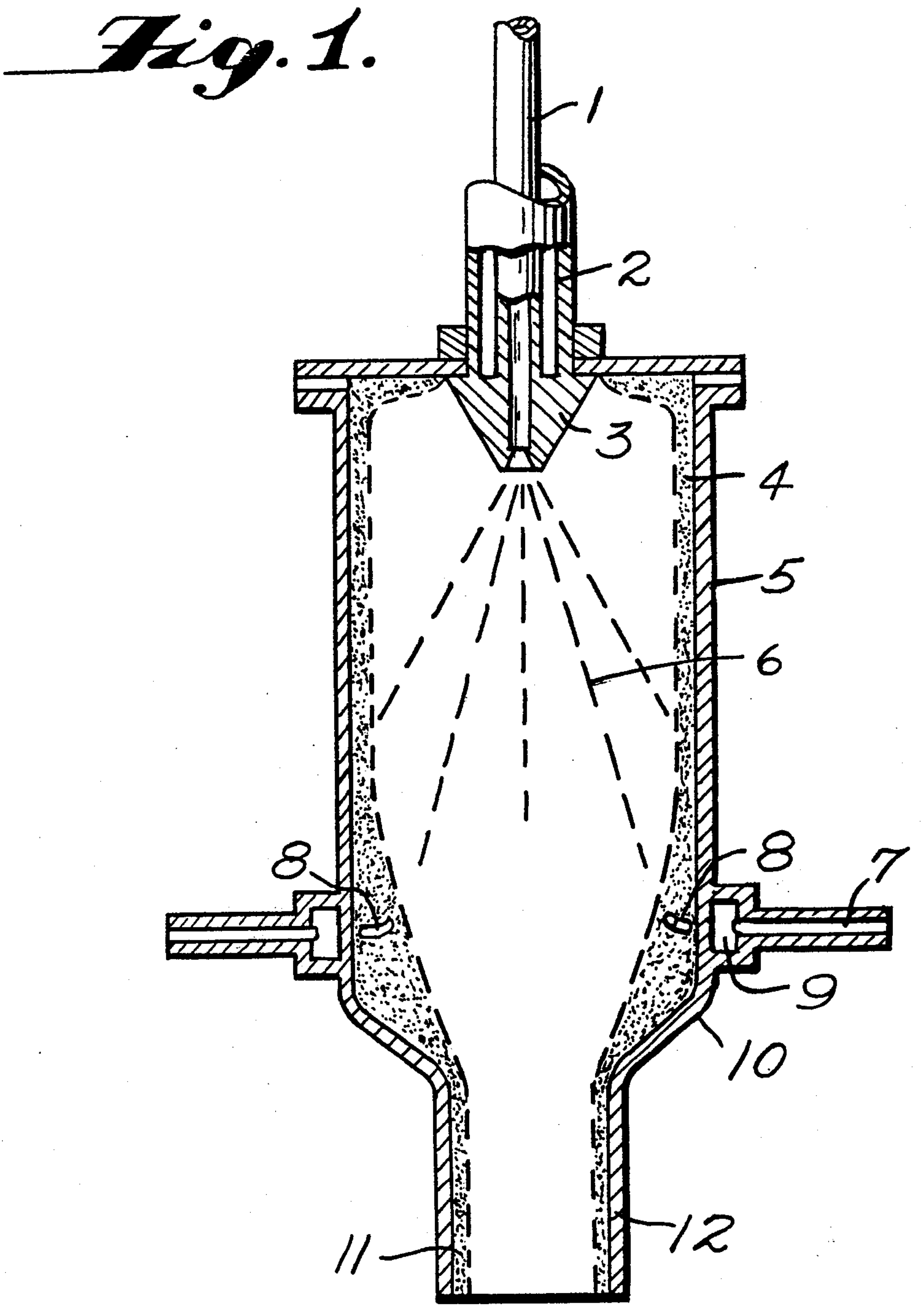
FIG. 1 is a vertical sectional elevation of one form of apparatus suitable for carrying out the process of the invention.

It has now been found that three identical substituents can be introduced into cyanuric chloride in the presence of an acid binding agent in a very short time and there can be recovered very pure trisubstituted s-triazine if liquid cyanuric chloride which is preferably free from chlorine and cyanogen chloride is sprayed into a container at temperatures in its molten range, if necessary in the presence of an inert gas, through a nozzle, preferably a spray nozzle, which is located in the head of a tubular container, during which this tubular container is closed or closeable at the top and downward constricted breast shaped to a discharge opening and with which the other reactant component or components discharge through one or preferably several nozzles, preferably polished steel nozzles, which are located above the constriction and consist of one or more tangential spray agencies arranged in one or more rows which are arranged slightly above in the direction of the upper closing device or are arranged in the direction of the nozzle located in the upper portion and form a liquid layer along the entire chamber walls up to the nozzle for the cyanuric chloride, whereby the density of this layer at the breast shaped restriction is greater than at the rest of the chamber walls, and in which the sprayed cyanuric chloride enters.

The liquid cyanuric chloride is preferably introduced into the nozzle through a heated conduit.

By using the described apparatus it is possible to so distribute the substituents, their solvents and the acid acceptor at the chamber walls that the liquid layer at the breast shaped constriction is thicker than at the remaining chamber walls.

By the expression used in the glass art: "breast shaped constriction" is meant a constriction which does not proceed steeply, but in a first S curve going from the wall of the tubular container to the discharge opening. Corresponding constrictions are also present in red wine bottles at the transition from the true bottle to the neck.

The constriction in the tubular container can preferably always begin where about 50% of the sprayed particles meet the liquid layer built up on the wall. Preferably this is the case in the lower third of the tubular container.

The size of the diameter of the discharge opening of itself is not critical. Naturally it depends on the viscosity of the medium being discharged and must have at least such a size that air can enter.

The discharge opening is preferably converted into a discharge tube which has any desired diameter, preferably however, the same diameter or larger than the discharge opening.

The nozzle or nozzles for the substituents, solvent and acid acceptor to be sure can be arranged at any place in the tubular container above the constriction, but preferably are located in the region directly above the breast shaped constriction.

As the tangentially arranged spray agencies, there can be used small tubes or nozzles as well as openings in the chamber walls or, with the presence of a feed ring, in its chamber walls.

Preferably there are used small tubes.

The tubular container described has the great advantage that it can be operated not only at an atmospheric pressure but also at reduced pressure. Thus without doing anything further it permits the adjustment proceeding from atmospheric pressure to reduced pressure of 0.01 bar.

At reduced pressure a portion of the solvent evaporates through which a cooling of the solution or suspension forming takes place. The mixing and reaction temperature in this way lets itself be held readily to a low level which is very essential for a continuous procedure.

As substituents there are employed known compounds suitable for the substitution of one or more chlorine atoms in cyanuric chloride.

Thus there can be used as amines in the process of the invention the monosubstituted amines of the formula $RNH_2$ mentioned in Tandon German Pat. No. 1,964,619. R can also be aryl. There can also be used the disubstituted amines of the formula

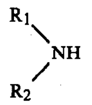

specified in German Pat. No. 1,695,117 where $R_1$, $R_2$ and $R_3$ are the same or different and are hydrogen, a lower alkyl, alkenyl or cycloalkyl group with 1-6 carbon atoms and wherein this group can be substituted by an OH-group or by a halogen atom, e.g., chlorine, bromine, fluorine, or interrupted by an O or S atom wherein $R_1$ and $R_2$ together with the adjacent N-atom can also form a pyrrolidino, morpholino or piperidino group, as well as the α-aminonitriles of the formula

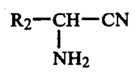

known for this purpose in which $R_2$ is alkyl group with 1-3 carbon atoms, see German Pat. No. 1,670,541 and related Schwarze U.S. Pat. No. 3,505,325 as well as the disubstituted α-aminonitriles of the formula

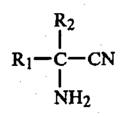

in German Pat. No. 1,670,528 in which $R_1$ and $R_2$ are the same or different and stand for hydrogen or a straight or branched alkyl or alkenyl group which in a given case is substituted by —OH, —OR or —SR groups, R hereby means a lower alkyl group with 1-4 carbon atoms. However, $R_1$ and $R_2$ can be straight or branched alkyl groups with 1-8 carbon atoms and can be joined together to form a 3-7 member ring. The entire disclosures of German Pat. No. 1,670,528, German Pat. No. 1,670,541 and Schwarze U.S. Pat. No. 3,505,325 are hereby incorporated by reference and relied upon.

Illustrative examples of suitable amines an α-aminonitriles are ammonia, methylamine, ethylamine, propylamine, butylamine, amylamine, hexylamine, isopropylamine, sec. butylamine, methoxypropylamine, methylthioethylamine, hydroxyethylamine (ethanolamine), allylamine, ethoxyethylamine, methoxyethylamine, methylthiopropylamine, butenylamine, cyclopropylamine, cyclobutylamine, cyclohexylamine, chloroethylamine, diallyl amine, dimethylamine, diethylamine, dipropylamine, diisopropylamine, dibutylamine, diamylamine, dihexylamine, methylethylamine, dicyclohexylamine, gamma-isopropoxypropylamine, diethanolamine, propanolamine, methallylamine, ethylpropylamine, morpholine, pyrrolidine, piperidine, methyl cyclohexyl amine, 2-aminopropionitrile, 2-aminobutyrnitrile, 2-aminovaleronitrile, 2-amino-3-methylbutyronitrile, 2-aminocapronitrile, 2-aminocaprilonitrile, 2-methyl-2-aminopropionitrile, 2-methyl-2-aminobutyronitrile, 2,3-dimethyl-2-aminobutyronitrile, 2,3-dimethyl-2-amino-butene-3-nitrile, 2-aminocyclopropyl nitrile, 2-aminocyclopentyl nitrile, 2-aminocyclohexyl nitrile, 2-aminocycloheptyl nitrile, 2-amino-4-methylthiobutyronitrile, 2-amino-pentene-3-nitrile, aniline, p-toluidine, o-toluidine, alpha-naphthyl amine, beta-naphthyl amine, N-methyl aniline, diphenyl amine.

It is also possible to react aminostilbene disulfonic acids and similar derivatives with cyanuric chloride according to the process of the invention and thereby obtain optical brightness.

As sulfur containing substituents which can be used according to the process of the invention there can be employed the mercaptans of the general formula H—S—R or mercaptides of the formula M—S—R mentioned in German Pat. No. 1,670,585 where R is a cycloalkyl, alkenyl, aralkyl or alkyl group with 1-18, preferably 1, carbon atoms which can be substituted by one or more alkoxy or alkyl mercapto groups with 1 to 4 carbon atoms and in which M is an alkali metal, e.g., sodium or potassium, or silver atom or is one valence of a mercury, zinc or lead atom. Also there can be used alkali metal hydrosulfides such as sodium hydrogen sulfide or potassium hydrogen sulfide.

Examples of mercaptans and mercaptides are methyl mercaptan, ethyl mercaptan, n-octyl mercaptan, allyl mercaptan, benzyl mercaptan, cyclohexyl mercaptan, octadecyl mercaptan, n-butyl mercaptan, isobutyl mercaptan, sec. butyl mercaptan, methallyl mercaptan, methylthiomethyl mercaptan, butylthioethyl mercaptan, methoxyethyl mercaptan, methoxymethyl mercaptan, butoxymethyl mercaptan, crotyl mercaptan, lauryl mercaptan, cyclopentyl mercaptan and the corresponding mercaptides such as sodium methyl mercaptide, sodium ethyl mercaptide, sodium octyl mercaptide, sodium hexadecyl mercaptide, sodium octadecyl mercaptide, sodium benzyl mercaptide, sodium allyl mercaptide, potassium methyl mercaptide, potassium hexadecyl mercaptide, potassium octadecyl mercaptide, potassium benzyl mercaptide, silver methyl mercaptide, mercury di(methyl mercaptide), zinc di(methyl mercaptide), lead di(methyl mercaptide).

There can also be used alcohols or alcoholates of the formula R—OH of R—OM where R is an alkyl, cycloalkyl, alkenyl or aralkyl group with 1-18 carbon atoms and where M is an alkali atom, e.g., sodium or potassium. Thus there can be used methanol, ethanol, isobutanol, pentanol, isopentanol, 2-methyl-butan-1-ol, 2,2-dimethyl-pentanol-1, propanol, isopropyl alcohol, butanol, 2-chloroethanol, 3-chloropropanol-1, 2-methoxyethanol, hexanol, octanol, octadecanol, 2-ethoxyethanol, 2-propoxyethanol, 2-n-butoxyethanol, anisyl alcohol, decanol, lauryl alcohol, allyl alcohol, 2 or 3-methoxypropanol, 3-ethoxypropanol-1, 3-methoxybutanol-1, methallyl alcohol, crotyl alcohol, 2-(2-methoxyethoxy)ethanol, 2-ethylmercaptoethanol, 2-phenoxyethanol, oleyl alcohol, benzyl alcohol, cyclohexylmethanol, 2-butene-1-ol, propargyl alcohol, sec. butanol, hexanol-2 sodium methylate, potassium methylate, sodium ethylate, cyclopentanol, potassium ethylate, sodium butylate, sodium octadecanoxide, sodium allylate, sodium benzylate, 1-methoxypropanol-2, cyclohexanol, 2-methylcyclohexanol, 1,3-diethoxypropanol-2, 3-methylbutanol-2.

There can also be employed phenolates of alkali metals, e.g., sodium phenolate, potassium phenolate, sodium cresylate.

Furthermore there can also be used alkali or ammonium azides of the formula $MeN_3$, e.g., sodium azide or potassium azide or $(NH_4)N_3$.

Likewise thiocyanate compounds of the formula R—SCN in which R is an alkyl group with 1-6 carbon atoms can be introduced quickly according to the process of the invention and with very good substitution rates. Examples of such thiocyanates are methyl thiocyanate, ethyl thiocyanate, butyl thiocyanate or hexyl thiocyanate.

As acid binding agents, there can likewise be used those known in the art, e.g., alkali hydroxides such as NaOH or KOH or alkali carbonates and bicarbonates such as sodium carbonate, potassium carbonate, sodium bicarbonate, potassium bicarbonate, e.g., see German Pat. No. 1,964,619.

There can also be employed organic bases such as collidine or pyridine as acid acceptors.

There can also be employed an additional molecule of the amine used for the reaction for acid binding, see French Pat. No. 1,239,784, the entire disclosure of which is hereby incorporated by reference and relied upon.

Since the cyanuric chloride is present in liquid form, it is not necessary to employ a solvent for it, however, it is favorable that the reaction of the amine or aminonitrile takes place in the presence of a carrier liquid. This solvent can be water or an organic liquid, such as a hydrocarbon such as toluene, an aliphatic chlorohydrocarbon such as methylene chloride or a ketone such as acetone or methyl ethyl ketone.

For the rest the temperatures and pH values given for the monosubstitution in the above-mentioned patents can be used.

A suitable apparatus for the introduction of the three substituents is described and claimed in U.S. Hentschel application Ser. No. 94,803, filed Nov. 15, 1979 and entitled "Apparatus For Bringing Liquids In Contact", which is operated in the following manner.

As shown in FIG. 1, the liquid cyanuric chloride in supply line 1 is led through a coaxial heater 2 via a unary or binary nozzle 3 into the mixing chamber 5, i.e., the tubular container 5.

Figure 2:
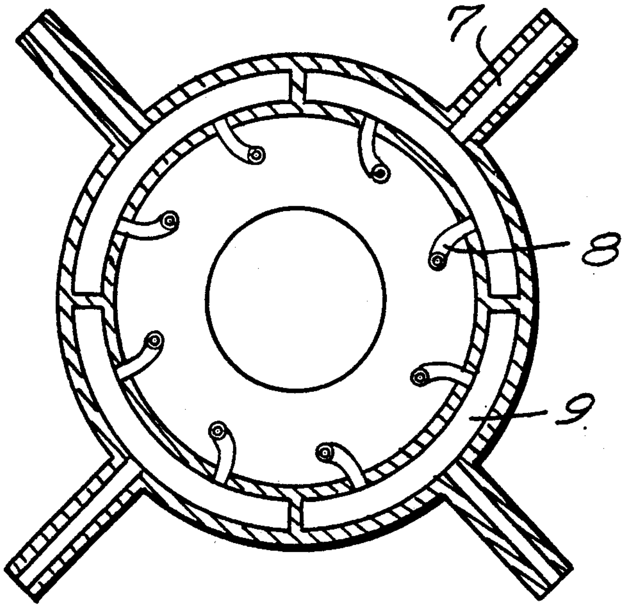
FIG. 2 is a cross-sectional view along the line 2—2 of FIG. 1.

The components being brought into contact with the sprayed material goes through separate lines 7 into a distribution ring having separate chamber segments 9, see also FIG. 2. The components are injected tangentially from these chamber segments via the slightly upwardly directed spray systems into the mixing chamber 5.

When using only one supply and only one opening into the mixing chamber 5, the supply 7 passes directly into the opening 8 and the segmented chamber 9 is eliminated.

Besides the component in the circumferential direction, the liquid jet has a velocity component in the axial direction. Therethrough the liquid reaches the wall of the mixing chamber 5. There it builds a liquid layer 4.

If different liquids are supplied through the supply lines 7, 8 and 9 into the mixing chamber 5, there occurs here an intensive thorough mixing of the supplied liquids, whose intensity can be increased still more by introducing a gas or vapors of the solvent via the spray system 8.

The cyanuric chloride leaving the nozzle 3 is sprayed into the liquid layer 4. The spray angle for the cyanuric chloride sprayed out of nozzle 3 can be between 15° and 150°, preferably between 15° and 120°.

The shape of the spray varies from hollow or solid cone up to an unarranged mist, according to the type of nozzle.

With the entering of the spray particles 6 solidify and/or the sprayed cyanuric chloride dissolves in the liquid layer. The energy brought in is given up to the liquid layer, independent of the pressure in the tubular container.

The discharging mixture which leaves the tubular container 5 through the discharge opening 12 goes to the container 14 which can be connected if desired detachably, either directly or indirectly via line 13 to the discharge opening 12 of the container 5.

Figure 3:
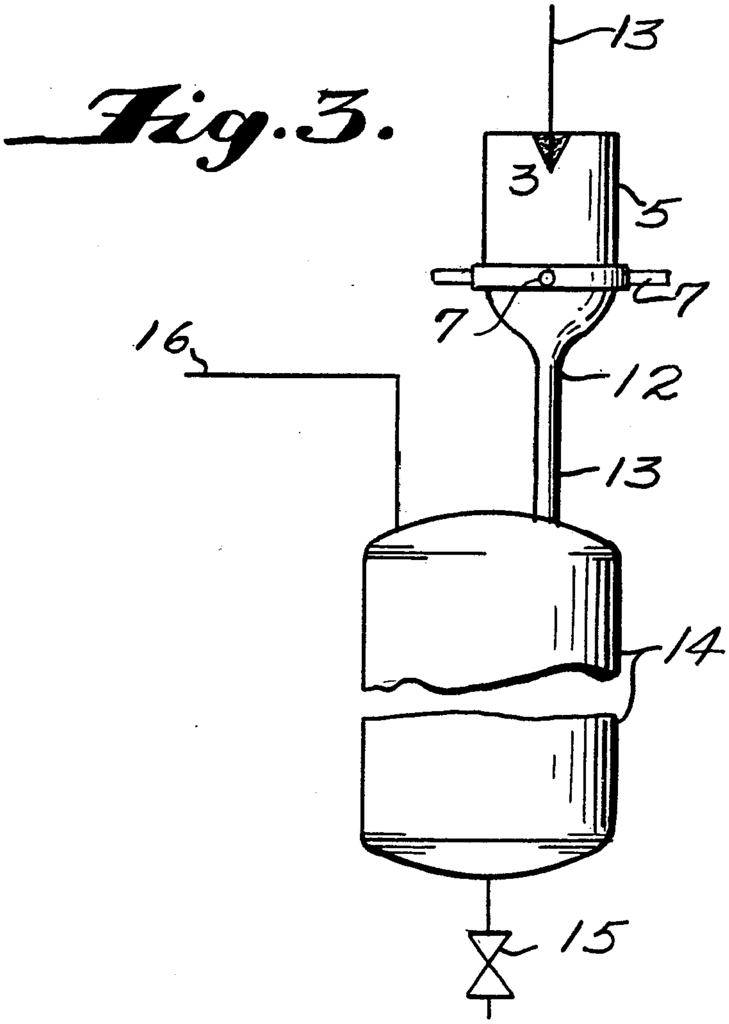
FIG. 3 is a schematic view of apparatus for carrying out the invention.

In this way it is possible to establish any desired pressure, i.e., any reduced or excess pressure, in the tubular container 5 and container 14 through known apparatus which is connected with the container 14 via line 16, see FIG. 3. (However, the known apparatuses for regulating the pressure are not shown in FIG. 3.)

The mixture is withdrawn at the discharge valve 15. The container 14, however, can in a given case also serve as reaction container for a further treatment or reaction.

However, it is also possible to apply reduced or superatmospheric pressure directly into the discharge line 13 through the known apparatuses and to transport away in known manner the discharging mixture from line 13 while eliminating an intermediate connection from container 14.

The apparatuses 5 and 14 shown in FIGS. 1 and 3, in a given case also line 13, can be heated or cooled in known manner, according to the requirements, see, e.g., Ullmann, Enzyklopädie technischen Chemie, Vol. 1, 3rd Edition, 1951, pages 743–744 and 769–770.

Likewise there can be used for this purpose the known construction materials, loc. cit.

The volume of the tubular container 5 is determined by the properties of the liquid used whereby the path of the sprayed particles 6 up to the imprignement on the liquid layer 4 should be held as short as possible.

Through this it is possible to carry out relatively large throughputs in a very small tubular container, e.g., the volume in Example 1 is about 0.5 liters. By establishing a specific pressure, e.g., a reduced pressure in mixing chamber 5, the heat energy and heat of reaction of the sprayed cyanuric chloride in contact with the liquid layer can be removed.

The product produced leaves the mixing chamber through the discharge outlet 12.

To improve the formation of the liquid layer the spray systems 8 tangential to the mixing chamber are directed slightly upwardly. The exact angle of bending is so adjusted according to the solvent that the liquid layer reaches up to the nozzle, but does not touch it.

Through the breast shaped constriction and the thicker liquid layer produced at this wall position thereby there results, despite the outlet opening, that the remaining chamber walls always are covered with a uniform, i.e., uninterrupted layer of liquid. Through this there is guaranteed a high mixing velocity.

The spray cone of the liquid cyanuric chloride is designated by the member 6.

The number of inlet lines 7 depends on the particular case.

Thus in feeding in the components one supply line is sufficient, however, for better distribution of these components there has also proven as desirable to use several supply lines, see for example FIG. 2; even using several liquids which also can be simultaneously introduced as a mixture the distribution ring described for example in FIG. 2 is suitable, in a given case there can be connected a further reaction space.

Liquid cyanuric chloride can be obtained according to known process, e.g., according to Geiger, German Pat. No. 2,322,636 and related Geiger U.S. Pat. No. 3,925,377. The entire disclosure of the Geiger U.S. patent is hereby incorporated by reference and relied upon.

Preferably according to the process of the invention there is employed a liquid cyanuric chloride whose temperature is 170° C. and which is free from chlorine and cyanogen chloride. For freeing from chlorine and cyanogen chloride known processes are suitable, as, e.g., dephlegmatization.

The s-triazines which have the same three substituents produced according to the process of the invention can be produced continuously in a very simple manner and in very high yields and purities.

Unless otherwise indicated all parts and percentages are by weight.

The process can comprise, consist essentially of or consist of the steps set forth and the materials can comprise, consist essentially of or consist of those set forth.

Trisubstituted s-triazines are employed in the fields of lubricant and rubber technology as well as in the technology of polymer production.

The invention will be further explained through the following examples.

DESCRIPTION OF THE PREFERRED EMBODIMENTS

EXAMPLE 1

Liquid cyanuric chloride at about 170° C. was led via the heated supply line 1 into the unary nozzle 3. The nozzle had a bore of 0.8 mm and a spray angle of about 78°. The supply pressure of the melt was 4 bar. There were sprayed through the nozzle 45 kg/h of cyanuric chloride into the mixing chamber 5. The mixing chamber 5 had a diameter of 80 mm and atmospheric pressure prevailed in it.

Methylene chloride in an amount of 300 liters/h via two opposed supply lines 7 via four small tubes 8 reached the mixing chamber 5 and through the other supply lines 7 260 l/h of an aqueous sodium hydrogen sulfide solution which contained 62 kg of 85% NaHS were introduced into the mixing chamber. The temperature of the discharging reaction mixture was about 35° C. After addition of 20% hydrochloric acid to a pH of 2 the methylene chloride was distilled off, the precipitate filtered off, washed with water and dried in a vacuum at about 70° C. There was a nearly quantitative yield of trimercapto-s-triazine.

EXAMPLE 2

Liquid cyanuric chloride at about 170° C. is led via the heated supply line 1 into the unary nozzle 3. This nozzle 3 has a bore of 0.8 mm and a spray angle of about 78°. The supply pressure of the liquid cyanuric chloride was 4 bar. There were sprayed 44.7 kg/h of liquid cyanuric chloride through the nozzle 3 into the mixing chamber 5. This mixing chamber 5 has a diameter of 80 mm and atmospheric pressure prevailed in it.

Acetone in an amount of 455 l/h via two opposed supply lines 7 via four small tubes 8 reached the mixing chamber 5 and through the other two supply lines 7 there were introduced into the mixing chamber 230 l/h of aqueous sodium phenolate solution in which there were dissolved 85 kg of sodium phenolate.

The discharging reaction mixture had a temperature of about 27° C. The suspension was diluted with water, filtered, washed with water and dried in a vacuum at 70° C. The yield of triphenoxy-s-triazine was 96%.

What is claimed is:

1. A process for the replacing the three chlorine atoms of cyanuric chloride by reacting cyanuric chloride with a compound which reacts with the chlorine atoms of cyanuric chloride in the presence of an acid binding agent comprising spraying cyanuric chloride downwardly and outwardly at a temperature in its molten range from the upper portion of a tertical tubular zone closed at the top thereof to contact and mix with the other compound which forms a liquid layer defining said tubular zone, constricting said layer in breast-shaped manner downwardly below the place of entry of the cyanuric chloride into the tubular zone to form a narrower discharge opening, discharging said other compound as a spray tangentially to said layer and directed slightly upwardly in the direction of the closed top above said constriction and below the point of introduction of the cyanuric chloride and thereby forming said liquid layer along the entire tubular zone to the point of introduction of the cyanuric chloride, whereby the thickness of said layer where it is formed into a breast-shaped constriction is greater than it is in the remainder of the tubular zone.

2. The process of claim 1 wherein the liquid cyanuric chloride employed is free from chlorine or cyanogen chloride.

3. A process according to claim 1 wherein there is employed an amine which is a monosubstituted amine of the formula $RNH_2$ or a disubstituted amine of the formula

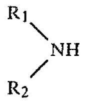

where R, $R_1$ and $R_2$ are hydrogen, lower alkyl, lower alkenyl or cycloalkyl groups with 1-6 carbon atoms or such groups substituted by OH or halogen or such groups interrupted in the chain by an O or S atom or are aryl or $R_1$ and $R_2$ together with the adjacent nitrogen atom form a pyrrolidino, morpholino or piperidino group and the aminonitrile has the formula

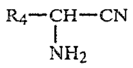
or
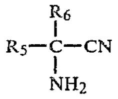

where $R_4$ is an alkyl group with 1 to 3 carbon atoms and $R_5$ and $R_6$ are lower alkyl or alkenyl groups with 1 to 8 carbon atoms or such groups substituted by —OH, —$OR_7$ or $SR_7$ where $R_7$ is lower alkyl of 1 to 8 carbon atoms or $R_5$ and $R_6$ are joined together to form a 3 to 7 member ring.

4. A process according to claim 2 wherein there is employed an amine of the formula $RNH_2$ or

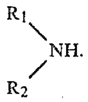

5. A process according to claim 4 where R, $R_1$ and $R_2$ are all other than aryl.

6. A process according to claim 5 wherein none of R, $R_1$ and $R_2$ is hydrogen.

7. A process according to claim 5 wherein R, $R_1$ and $R_2$ are lower alkyl.

8. A process according to claim 7 wherein the amine has the formula $RNH_2$.

9. A process according to claim 2 wherein there is employed an aminonitrile of the formula

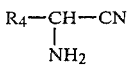
or
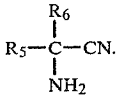

10. A process according to claim 9 where $R_4$, $R_5$ and $R_6$ are lower alkyl or alkenyl groups.

11. A process according to claim 10 wherein $R_4$, $R_5$ and $R_6$ are lower alkyl groups.

12. A process according to claim 9 wherein there is employed an aminonitrile of the formula

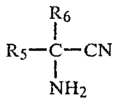

and $R_5$ and $R_6$ are joined to form a 3 to 7 member ring.

13. A process of claim 1 including reducing the pressure to between below atmospheric pressure and 0.01 bar and thereby lowering the mixing and reaction temperature.

14. A process according to claim 1 comprising discharging the reaction mixture formed to another container adapted for use at subatmospheric of superatmospheric pressure.

15. The process of claim 1 wherein there is employed a mercaptan of the formula H—S—R or a mercaptide of the formula M—S—R in which R is cycloalkyl, alkenyl, aralkyl or alkyl with 1-18 carbon atoms or such a mercaptide substituted with an alkoxy or alkylmercapto group containing 1-4 carbon atoms and where M is an alkali metal atom, silver atom or a valence of mercury, zinc or lead atom.

16. The process of claim 15 wherein the compound employed is a mercaptan of the formula H—S—R.

17. The process of claim 16 where R is alkyl.

18. The process of claim 15 wherein the compound employed is a mercaptide of the formula M—S—R.

19. The process of claim 18 where R is alkyl.

20. The process of claim 19 where M is an alkali metal atom.

21. The process of claim 20 where the alkali metal atom is the sodium atom.

22. A process according to claim 1 wherein there is employed an alkali metal hydrosulfide as a reactant.

23. A process according to claim 22 wherein the alkali metal is sodium.

24. A process according to claim 1 wherein there is employed an alkali metal phenolate as a reactant.

25. A process according to claim 24 wherein the phenolate is sodium phenolate.

26. A process according to claim 1 wherein there is employed an alcohol or alcoholate of the formula R—OH or R—OM where R is an alkyl, cycloalkyl, alkenyl or aralkyl having 1-18 carbon atoms and in which M is an alkali metal.

27. A process according to claim 1 wherein there is employed an alkali metal azide of the formula $MeN_3$ or $(NH_4)N_3$.

28. A process according to claim 1 wherein there is employed a thiocyanate of the formula R—SCN where R is an alkyl group having 1-6 carbon atoms.

* * * * *